(12) United States Patent
Moretto et al.

(10) Patent No.: US 9,506,867 B2
(45) Date of Patent: Nov. 29, 2016

(54) SPECTROSCOPIC ANALYSIS OF NUTRIENT MATERIALS FOR USE IN A CELL CULTURE PROCESS

(71) Applicant: Biogen MA Inc., Cambridge, MA (US)

(72) Inventors: Justin Moretto, Apex, NC (US); Kelly Wiltberger, Cary, NC (US)

(73) Assignee: Biogen MA Inc., Cambridge, MA (US)

( * ) Notice: Subject to any disclaimer, the term of this patent is extended or adjusted under 35 U.S.C. 154(b) by 69 days.

(21) Appl. No.: 14/103,801

(22) Filed: Dec. 11, 2013

(65) Prior Publication Data
US 2014/0185033 A1    Jul. 3, 2014

Related U.S. Application Data

(60) Provisional application No. 61/735,981, filed on Dec. 11, 2012.

(51) Int. Cl.
*G01J 3/44* (2006.01)
*G01N 21/65* (2006.01)

(52) U.S. Cl.
CPC *G01N 21/65* (2013.01); *G01J 3/44* (2013.01)

(58) Field of Classification Search
CPC ................... G01J 3/44; G01N 21/65
See application file for complete search history.

(56) References Cited

U.S. PATENT DOCUMENTS

| | | | |
|---|---|---|---|
| 7,521,203 B2 | 4/2009 | Lin et al. | |
| 8,224,415 B2 | 7/2012 | Budiman | |
| 2004/0180379 A1 | 9/2004 | Van Dunye et al. | |
| 2005/0089993 A1 | 4/2005 | Boccazzi et al. | |
| 2008/0299539 A1 | 12/2008 | Lee et al. | |
| 2009/0023804 A1 | 1/2009 | Baugh et al. | |
| 2009/0104594 A1 | 4/2009 | Webb | |
| 2009/0312851 A1 | 12/2009 | Mishra | |
| 2010/0256336 A1 | 10/2010 | Yuk et al. | |
| 2012/0123688 A1 | 5/2012 | Ramasubramanyan et al. | |
| 2012/0229796 A1* | 9/2012 | Priore | G01N 21/359 356/51 |
| 2013/0189723 A1 | 7/2013 | Felder et al. | |
| 2016/0025633 A1 | 1/2016 | Moretto et al. | |

FOREIGN PATENT DOCUMENTS

WO    WO 97/14430 A    4/1997

OTHER PUBLICATIONS

Li et al., "Using Surface-enhanced Raman Scattering (SERS) and Fluorescence Spectroscopy for Screening Yeast Extracts, a Complex Component of Cell Culture Media", Dec. 22, 2011, Journal of Raman Spectroscopy, 43, 1074-1082.*
Li et al., "Rapid Characterization and Quality Control of Complex Cell Culture Media Solutions Using Raman Spectroscopy and Chemometrics", May 20, 2010, Biotechnology and Bioengineering, vol. 107, No. 2, pp. 290-301.*
Seli et al., "Noninvasive Metabolomic Profiling of Embryo Culture Media using Raman and Near-infrared Spectroscopy Correlates with Reproductive Potential of Embryos in Women Undergoing in vitro Fertilization", Nov. 2007, Fertility and Sterility, vol. 88, No. 5, pp. 1350-1357.*
Shen et al., "Accurate and noninvasive embryos screening during in vitro fertilization (IVF) assisted by Raman analysis of embryos culture medium", Jan. 30, 2012, Laser Physic Letters, pp. 322-328.*
Rodrigues, Lidiany Karla Azevedo et al. "Assessment of enamel chemistry composition and its relationship with caries susceptibility". Lasers in Dentistry XI, Proceedings of SPIE vol. 5687, 2005, pp. 132-139.*
Abu-Absi et al., Real time monitoring of multiple parameters in mammalian cell culture bioreactors using an in-line Raman spectroscopy probe. Biotechnol Bioeng. May 2011;108(5):1215-21. doi: 10.1002/bit.23023. Epub Dec. 22, 2010.
Cline et al., Anomalously Slow Electron Transfer at Ordered Graphite Electrodes: Influence of Electronic Factors and Reactive Sites. J. Phys. Chem. 1994;98(2):5314-5319.
Houde et al., Determination of protein oxidation by mass spectrometry and method transfer to quality control. J Chromatogr A. Aug. 11, 2006:1123(2):189-98. Epub May 22, 2006.
Jackson et al., Surface-enhanced Raman scattering on tunable plasmonic, nanoparticle substrates. PNAS. Dec. 28, 2004;101(52):17930-17935.
Jia et al., Label-free fluorometric assay for acetylcholinesterase and inhibitor screening based on supramolecular assemblies. Anal Methods. 2013;5:5431-5436.
Lee et al., Characterization of raw material influence on mammalian cell culture performance: chemometrics based data fusion approach. Accessed via http://focapo.cheme.cmu.edu/2012/proceedings/data/papers/085.pdf on Dec. 12, 2011. 6 pages.
Lee et al., Data fusion-based assessment of raw materials in mammalian cell culture. Biotechnol Bioeng. Nov. 2012;109(11):2819-28. doi: 10.1002/bit.24548, Epub May 28, 2012.
Martens et al., Extended multiplicative signal correction and spectral interference subtraction: new preprocessing methods for near infrared spectroscopy. J Pharm Biomed Anal. 1991;9(8):625-35.
Molloy et al., Human furin is a calcium-dependent serine endoprotease that recognizes the sequence Arg-X-X-Arg and efficiently cleaves anthrax toxin protective antigen. J Biol Chem. Aug. 15, 1992;267(23):16396-402.
Mungikar et al., Use of In-line Raman Spectroscopy as a Nondestructive and Rapid Analytical Technique to Monitor Aggregation of a Therapeutic Protein. American Pharmaceutical Review. Nov. 2010. 78-83.
Raman et al., A New Type of Secondary Radiation. Nature. Mar. 1928;121:501-502.

(Continued)

*Primary Examiner* — Michael A Lyons
(74) *Attorney, Agent, or Firm* — Wolf, Greenfield & Sacks, P.C.

(57) ABSTRACT

In some embodiments, aspects of the disclosure relate to methods of evaluating cell culture materials, for example, nutrient materials, or other materials that can be used in cell culture media.

14 Claims, 5 Drawing Sheets

(56) References Cited

OTHER PUBLICATIONS

Ryan et al., Prediction of cell culture media performance using fluorescence spectroscopy. Anal Chem. Feb. 15, 2010;82(4):1311-7. doi: 10.1021/ac902337c.

Thomson et al., Resurrecting ancestral alcohol dehydrogenases from yeast. Nat Genet. Jun. 2005;37(6):630-5. Epub May 1, 2005.

Wen et al., Application of Raman Spectroscopy in Biopharmaceutical Manufacturing. Raman. Jun. 2010. 46-53.

Witjes et al., Automatic correction of peak shifts in Raman spectra before PLS regression. Chemo. Intell. Lab. Systems. Aug. 2000;52(1):105-116.

Berry et al., Cross-scale predictive modeling of CHO cell culture growth and metabolites using Raman spectroscopy and multivariate analysis. Biotechnol Prog. Mar.-Apr. 2015;31(2):566-77. doi:10.1002/btpr.2035. Epub Dec. 29, 2014.

Chen et al., Effects of elevated ammonium on glycosylation gene expression in CHO cells. Metab Eng. Mar. 2006;8(2):123-32. Epub Dec. 27, 2005.

Moretto et al., Process Raman Spectroscopy for In-Line CHO Cell Culture Monitoring. Apr. 2011. American Pharmaceutical Review.

\* cited by examiner

Figure 1. Raman spectrum of a sample between 800 and 1500 cm-1.

Figure 2. Lactate Production Integral in Various Yeastolate Lots (Actual vs. Predicted)

Figure 3. Day 8 pH in Various Yeastolate Lots (Actual vs. Predicted)

Figure 4. Peak 5 in Various Yeastolate Lots (Actual vs. Predicted)

Figure 5. Principal Component Analysis (PCA) of Pluronic Lots

SPECTROSCOPIC ANALYSIS OF NUTRIENT MATERIALS FOR USE IN A CELL CULTURE PROCESS

RELATED APPLICATIONS

This application claims the benefit under 35 U.S.C. §119 (e) of U.S. provisional application No. 61/735,981, filed Dec. 11, 2012, the content of which is hereby incorporated by reference in their entirety.

FIELD OF THE INVENTION

The present disclosure relates to the field of spectroscopic analysis of nutrient materials.

BACKGROUND OF THE INVENTION

The production of biological materials in culture medium often involves expensive starting material, fine tuning of the balance of culture components and metabolites, and complex time-consuming synthesis and purification steps. The production process can fail at any stage due to unbalance in the various components and metabolites in the culture medium. However, failure often is not detected until late in the production process when final yields are evaluated. This can result in an expensive waste of time and material.

SUMMARY OF THE INVENTION

In some embodiments, aspects of the disclosure relate to methods of evaluating cell culture media, nutrient materials, and other similar materials. In some embodiments, methods disclosed herein are useful monitoring or assessing quality of biological materials. For example, methods are provided that involve performing a Raman spectroscopic analysis on a sample (e.g., a sample of a nutrient material) to obtain a Raman spectrum and identifying, based the Raman spectrum, quality of the sample (e.g., quality of the nutrient material or quality of a cell culture grown using the nutrient material). In some embodiments, methods provided herein further involve differentiating a sample from a second sample based on a difference between the Raman spectrum of the sample and a second Raman spectrum of the second sample. For example, the methods may further involve differentiating a nutrient material from a second nutrient material based on a difference between the Raman spectrum of the nutrient material and a second Raman spectrum of the second nutrient material. In some embodiments, methods provided herein may be used for purposes of assessing multiple (e.g., 2, 3, 4, 5, 10 or more) different samples for identifying differences between or among samples and, in some cases, relating such differences to sample quality.

In some embodiments, methods provided herein may further involve performing a comparison of at least a portion of a Raman spectrum with at least a portion of a model Raman spectrum. In some embodiments, methods provided herein further involve performing a comparison of data obtained from a Raman spectrum with model data. In some embodiments, methods provided herein involve accepting or rejecting a nutrient material for use in a cell culture process based on a result of a comparison of at least a portion of the Raman spectrum with at least a portion of a model Raman spectrum.

In some embodiments, methods provided herein further involve performing first and second spectroscopic analyses on samples (e.g., samples of nutrient materials) to obtain first and second spectra and performing a data fusion analysis to evaluate the Raman spectra. In some embodiments, the first spectroscopic analysis is a Raman analysis and the second spectroscopic analysis is a Nuclear Magnetic Resonance (NMR) analysis, a Near Infrared Spectroscopy (NIR) or other non-Raman analysis.

In some embodiments, methods provided herein further involve identifying a value of a quality parameter based on a Raman spectrum. In some embodiments, the quality parameter relates to a nutrient material or to a cell culture grown using the nutrient material. In some embodiments, the quality parameter is a pH (e.g., Day 8 pH). In some embodiments, the quality parameter is a peak of a chromatograph (e.g., Peak 5) of an elution of a drug product produced by a cell culture correlates with the presence of certain protein isoforms. In some embodiments, the quality parameter is a Lactate Production Integral. In some embodiments, the methods involve predicting a value of the quality parameter based on a predictive least squares (PLS) predictive model.

In some embodiments, aspects of the disclosure relate to methods of evaluating a nutrient material. In some embodiments, methods provided herein involve performing a Raman spectroscopic analysis on a sample of a nutrient material to obtain a Raman spectrum; generating a model of the sample based on the Raman spectrum; and performing a comparison of the model of the sample with a reference model. For example, methods provided herein may involve performing a Raman spectroscopic analysis on a sample of the nutrient material to obtain a Raman spectrum; generating a Principal Component Analysis (PCA) model of the sample based on the Raman spectrum; and performing a comparison of the PCA model of the sample with a reference PCA model. In some embodiments, the methods further involve accepting or rejecting the nutrient material for use in a cell culture process based on a result of the comparison.

In some embodiments, performing the Raman spectroscopic analysis comprises performing Surface Enhanced Raman Spectroscopy (SERS). In some embodiments, performing the Raman spectroscopic analysis comprises performing ultraviolet (UV) Raman spectroscopy.

In some embodiments, a sample on which a Raman spectroscopic analysis is performed is in the form of a liquid, a gas or a solid. In some embodiments, a sample may contain a single component of interest (e.g., a single solute material) or may contain a mixture of different components of interest (e.g., a mixture of multiple different solutes.)

In one aspect, the disclosure provides methods of evaluating a culture material level in a culture medium. In some embodiments, the methods involve obtaining a Raman spectrum of a culture medium, parsing the Raman spectrum with a Raman signature of the culture material to identify peaks corresponding the culture material, and measuring the intensity of the identified peaks to evaluate the culture material level in the medium. In some embodiments, the method further comprises adjusting the culture material level if the level is outside a predetermined range.

In one aspect, the disclosure provides methods of evaluating a culture material level in a culture medium. In some embodiments, the methods involve obtaining a Raman spectrum of a culture medium, parsing the Raman spectrum with a Raman signature of the culture material to identify peaks corresponding the culture material, and measuring the intensity of the identified peaks to evaluate the culture material level in the medium.

DETAILED DESCRIPTION OF THE INVENTION

Certain nutrient materials that are suitable for use as nutrient platforms, nutrient supplements or growth modulators for cell culture processes may be complex, highly variable materials with many (e.g., upwards of 100) individual compounds. These nutrient materials, such as yeastolate, are often sold in lots that are offered as generally comparable. Yet despite this designation by the vendors, the different lots can be highly variable and can lead to significant changes in culture performance. In the case of pluronic F-68, as just one example, the vendor provides that each lot is a homogeneous mix of polymers that all match a specific profile within a specified degree of error. However, experience indicates that there are batch to batch differences of this material that are not being captured by conventional vendor qualifications, similar to the yeastolate batch to batch differences.

It is desirable to characterize the qualities of a material (e.g., a nutrient material or other material that can be used to support cell growth and or protein production in a cell culture, for example yeastolate, for example pluronic, for example another type of surfactant, or other material) with greater accuracy, so that the material can be selected for use in a cell culture process for which its qualities are well-suited, or rejected if its qualities are not a sufficient match for an intended use. Better characterizations of the qualities of materials (e.g., nutrient or other materials) would not only reduce costs (e.g., by reducing the number of cell cultures that must be discarded due to poorly performing nutrient materials), but also enhance quality of the cultured cells (e.g., by reducing batch-to-batch variations in the quality of the cultured cells). In addition, better characterizations of the qualities of materials (e.g., nutrient materials) would allow vendors to control their material (e.g., nutrient material) production processes in order to produce materials (e.g., nutrient materials) with the precise qualities desired by potential purchasers.

In addition, it is desirable to characterize the qualities of a material (e.g., a nutrient material) quickly and non-invasively. Characterization techniques that take long periods of time (e.g., weeks) or consume large amounts of material are less beneficial.

Figure 1:
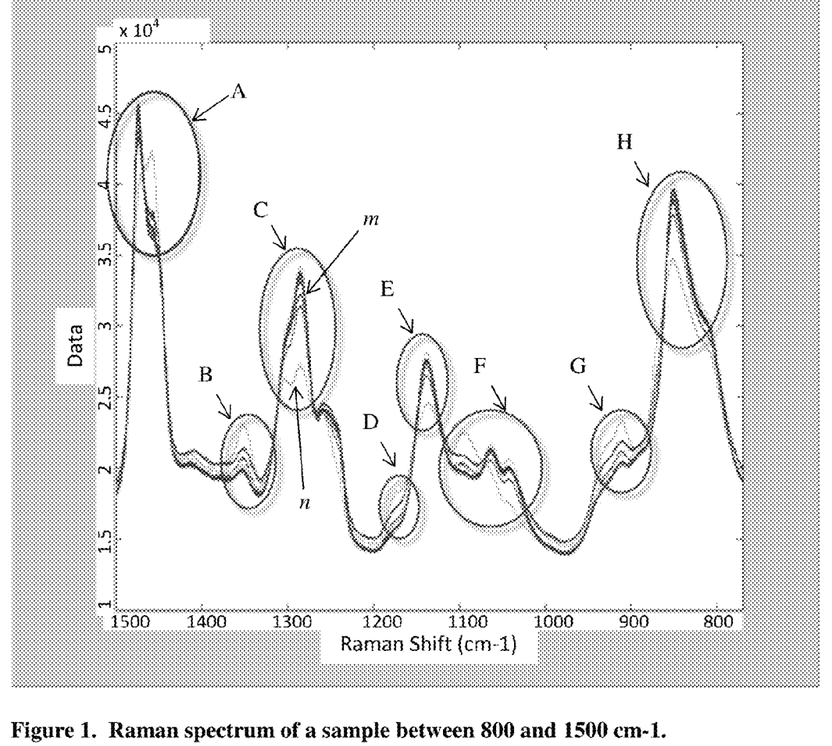
FIG. 1 illustrates a non-limiting embodiment of a Raman spectrum of several pluronic samples between 800 and 1500 cm$^{-1}$.

One aspect of the present disclosure relates to collecting and analyzing a Raman spectrum of a material (e.g., a nutrient material or other material, for example yeastolate or pluronic or other surfactant or other material). In some embodiments, attributes of a material's Raman spectrum may indicate qualities of the material and/or qualities of a cell culture grown using the material. For example, attributes of a Raman spectrum (or a portion thereof) that may be evaluated (e.g., correlated with one or more cell growth and/or protein production characteristics, for example to predict or indicate a quality of cell culture grown using a material, e.g., a nutrient material) may include the number of peaks of the spectrum, the number of peaks that exceed a threshold value, the relationships between the values of certain peaks, the shape of the spectrum, the position of one or more peaks (e.g., the relative position of two or more peaks), the shape of one or more peaks (e.g., peak height, peak width, area under the curve, or a combination of two or more thereof, for each peak), etc., or any combination of two or more thereof. In some embodiments, a Raman spectrum (or a portion thereof) can be evaluated by evaluating a combination of peak shape, peak location, and peak intensity (e.g., peak height) of one or more peaks. It should be appreciated that one or more attributes of a Raman spectrum (or a portion thereof) of a material of interest can be evaluated by comparing it/them to one or more attributes (e.g., corresponding attributes) for a Raman spectrum of a control or reference material (e.g., a material having known properties, for example a material known to support acceptable cell growth and/or protein production in a cell culture). It should be appreciated that different regions of a Raman spectrum may be evaluated for different materials. In some embodiments, an analysis may include a plurality of peaks (e.g., 2-10, for example 5-10, or more). In some embodiments, one or a few (e.g., 2, 3, or 4) peaks may be evaluated. It should be appreciated that different peaks or patterns of peaks in different regions of a Raman spectrum may be used for different materials. For example, as shown in FIG. 1, in some embodiments a region in Raman spectrum in the range of 750-1500 cm$^{-1}$ may have a series of peaks that can be used (e.g., individually or any combination of two or more peaks) to differentiate between types of a material (e.g., pluronic) and/or to identify the content of a sample of nutrient material (e.g., the content of oxyethylene in a sample).

Accordingly, an analysis can involve evaluating a peak number, peak intensity (height), peak position, peak shape, peak width, or any combination thereof for a material of interest within a defined wavenumber range of a Raman spectrum for that material. It should be appreciated that each chemical species within a complex mixture has its own unique Raman signature. This signature represents the collection of peaks (or peak attributes) which represent unique vibrational states of the chemical species within the mixture. In a complex mixture, many peaks can overlay to produce broad, non-discreet peaks which are best analyzed using one or more multivariate analytical techniques (e.g., to discriminate between relatively small informative changes and background noise when comparing two or more samples of the mixture. In some embodiments, an analysis can be simplified (and/or the sensitivity and/or specificity of an analysis can be increased) by evaluating a material of interest in a simple preparation (e.g., a homogeneous solution of the material of interest, or a solution of the material of interest in the presence of only one or a few and/or relatively low amounts of other materials). In some embodiments, an analysis can be simplified (and/or the sensitivity and/or specificity of an analysis can be increased) by restricting the analysis to a region of a spectrum that is more informative than other regions (e.g., a region that contains one or more informative peaks, for example peaks that have distinguishable sizes, shapes, positions, intensities, etc. for different types of materials).

It should be appreciated that techniques described herein can be used to distinguish between different types of materials (e.g., to confirm that a material being used is indeed the intended material), to confirm that a material has desired properties, or to determine whether a material has been degraded or otherwise modified (e.g., such that it may adversely impact cell growth and/or protein production using the material).

It should be appreciated that one or more attributes of a Raman spectrum of a material of interest can be associated with one or more qualities of a cell culture grown using the material. This information can then be used to predict one or more cell culture qualities based on an analysis of the Raman spectrum of a material (e.g., a new batch or lot of the same material) without actually testing the material in a cell culture. Non-limiting examples of qualities of a cell culture grown using a material (e.g., a nutrient material) that may be identified or predicted based on analysis of a Raman spectrum of the material (e.g., nutrient material) may include the cell culture's lactate production integral, Day 8 pH, or Peak 5. However, it should be appreciated that one or more other qualities of a cell culture (e.g., protein yield, for example the yield of a recombinant protein expressed by the cells) can be evaluated and associated with one or more attributes of a Raman spectrum of a cell culture material as aspects of the invention are not limited in this respect.

The lactate production integral may refer to the total lactate produced over the course of a cell culture run. The lactate production integral can be determined as the area under the curve produced when lactate values are plotted versus time for a cell culture (e.g., in a batch process). It should be appreciated that this value takes into account not only the instantaneous lactate value but also the historical values during the cell culture. This measure may be preferable to a discrete measure because the production integral normalizes for individual highs and lows and allows the analysis to focus on high overall lactate production of a cell culture. Though, in some embodiments, a discrete measure (e.g., at a particular time point) of lactate production may be used.

Day 8 pH (pH of a cell culture measured on day 8 (e.g., after initial inoculation)) has been shown through rigorous multivariate analysis to be an accurate indicator of the productivity of some cell culture processes. Thus, correlating the Raman attributes of one or more cell culture materials (e.g., pluroic or yeastolate) to the Day 8 pH of their respective cell culture processes allows for the prediction of future productivity.

Peak 5 refers to an additional quality parameter (e.g., a quality release criterion). In some embodiments, the intensity of a peak (for example the 5th peak—Peak 5) on a chromatograph of an elution of a drug product produced by a cell culture correlates with the presence of certain protein isoforms. In some embodiments, one or more of these isoforms are deleterious and unwanted. Accordingly, in some embodiments, cell culture material that has a Raman spectrum associated with the production of unwanted protein isoforms can be identified and discarded to avoid producing the unwanted protein isoforms.

It should be appreciated that one or more other quality parameters of a cell culture process and/or protein production process (e.g., titer, level of mannose, level of fucose, level of galactose, level of sialic acid, percent drop in viability, peak viable cell density (VCD), growth rate, or specific productivity) may be correlated with data obtained from the Raman spectrum of the cell culture's materials (e.g., nutrient materials or other cell culture materials).

Aspects of the present disclosure relate to collecting Raman spectra from two or more cell culture materials (e.g., nutrient materials), for example, two or more samples of a material, samples from two or more batches or lots of a material, samples of different materials, etc. and analyzing the spectra to determine whether there are significant differences between the materials. In some embodiments, analysis of the spectra may be used to indicate how the nutrient materials differ (e.g., what qualities of the nutrient materials differ, what qualities of cell cultures grown using the nutrient materials differ, and the value or significance of any such difference).

Another aspect of the present disclosure relates to collecting a Raman spectrum of a cell culture material (e.g., a nutrient material) and analyzing that spectrum to determine how the qualities of the material (or cell cultures grown using the nutrient material) relate to desired qualities. In some embodiments, the spectrum of the material may be compared to a model spectrum, such as a spectrum obtained from a material known to have the desired qualities. In some embodiments, data obtained by analyzing the spectrum of the material may be compared against a qualitative or quantitative model to determine whether the material is suitable for use in a cell culture process (e.g., whether the material should be accepted or rejected by a potential user).

Another aspect of the present disclosure relates to using quality parameters obtained by analyzing a Raman spectrum of a nutrient material to build a model of a desired nutrient material. For example, quality parameters such as the herein-described quality parameters (e.g., Day 8 pH, Lactate Production Integral, etc.) may be used. In some embodiments, the model may be a predictive model or a comparison model. For example, a partial-least squares (PLS) predictive model may be suitable in the case of yeastolate qualification, or a principal component analysis (PCA) comparison model may be used to separate differences in pluronic cell culture materials and to group the materials based on historical performance. However, it should be appreciated that any suitable multivariate analysis may be used to evaluate and compare Raman spectra obtained for different materials (e.g., different batches or lots of the same material).

In some embodiments, raw Raman spectrum data are trimmed to desired wavenumber (or Raman shift) regions. In some embodiments, an appropriate baseline algorithm is applied to Raman spectrum data (e.g., trimmed data). In some embodiments, the baseline algorithm is a weighted least squares type algorithm. In some embodiments, the algorithm uses an appropriate filter (e.g., a second order basis filter). In some embodiments, the algorithm is weighted (e.g., using power method weighting). In some embodiments, the algorithm uses an appropriate confidence limit (e.g., 0.99 confidence limit). In some embodiments, the algorithm uses a bottom alignment. In some embodiments, extended multiplicative signal/scatter correction (EMSC) is applied. In some embodiments, EMSC facilitates explicit compensation for variabilities (e.g., chemical variabilities) by including information about a major analyte and an interferent spectra in the estimation. In some embodiments, an EMSC utilizes the following equation: $z_i = z_0 b_i + K h i + 1 a_i + e_i$, as reported in Harald Martens, Edward Stark, Extended multiplicative signal correction and spectral interference subtraction: New preprocessing methods for near infrared spectroscopy, Journal of Pharmaceutical and Biomedical Analysis, Volume 9, Issue 8, 1991, Pages 625-635, ISSN 0731-7085, the contents of which are incorporated herein by reference in their entirety. In some embodiments, a principal component analysis (PCA) and/or partial-least squares (PLS) are built from the processed data. In some embodiments, data are centered (e.g., using mean centering). In some embodiments, data are standardized.

In some embodiments, a first order, quadratic, Savitsky-Golay derivative is applied to data. In some embodiments, a first order, quadratic, Savitsky-Golay derivative is applied to data using between 15 and 51 points for each sub-model. In some embodiments, a standard normal variance filter is applied. In some embodiments, data are trimmed to the pertinent wavenumber (or Raman shift) regions and mean centered in the same processing step. In some embodiments, a principal component analysis (PCA) and/or partial least squares (PLS) are built from the processed data. In some embodiments, data are centered (e.g., using mean centering). In some embodiments, data are standardized.

In some embodiments, Raman interference due to solvents or other components may be eliminated through baseline subtraction. In some embodiments, the herein-described models and Raman spectra collected from cell culture materials (e.g., nutrient materials) may be used to select cell culture materials (e.g., nutrient materials) for cell growth. The cell growth may be, for example, for protein production (e.g., for antibody production, for example for humanized antibody production). In some embodiments, cell growth may be that of a recombinant cell (e.g., bacterial, yeast, mammalian, or other cell type) that expresses a protein of interest. In some embodiments, a protein of interest may be, but is not limited to, anti-LINGO, anti-LINGO-1, interferon (e.g., interferon beta 1a-AVONEX), Abciximab (REOPRO®), Adalimumab (HUMIRA®), Alemtuzumab (CAMPATH®), Basiliximab (SIMULECT®), Bevacizumab (AVASTIN®), Cetuximab (ERBITUX®), Certolizumab pegol (CIMZIA®), Daclizumab (ZENAPAX®), Eculizumab (SOLIRIS®), Efalizumab (RAPTIVA®), Gemtuzumab (MYLOTARG®), Ibritumomab tiuxetan (ZEVALIN®), Infliximab (REMICADE®), Muromonab-CD3 (ORTHOCLONE OKT3®), Natalizumab (TYSABRI®), Omalizumab (XOLAIR®), Palivizumab (SYNAGISIO), Panitumumab (VECTIBIX®), Ranibizumab (LUCENTIS®), Rituximab (RITUXAN®), Tositumomab (BEXXAR®), and/or Trastuzumab (HERCEPTIN®). In some embodiments, the protein of interest is Natalizumab (TYSABRI®). In some embodiments, the protein of interest is a blood cascade protein. Blood cascade proteins are known in the art and include, but are not limited to, Factor VII, tissue factor, Factor IX, Factor X, Factor XI, Factor XII, Tissue factor pathway inhibitor, Factor V, prothrombin, thrombin, vonWillebrandFactor, kininigen, prekallikrien, kallikrein, fribronogen, fibrin, protein C, thrombomodulin, and antithrombin. In some embodiments, the blood cascade protein is Factor IX or Factor VIII. It should be appreciated that the methods are also applicable for uses involving the production of versions of blood cascade proteins, including blood cascade proteins that are covalently bound to antibodies or antibody fragments, such as Fc. In some embodiments, the blood cascade protein is Factor IX-Fc (FIXFc) or Factor VIII-Fc (FVIIIFc). In some embodiments, one or more proteins of interest are hormones, regulatory proteins and/or neurotrophic factors. Neurotrophic factors are known in the art and include nerve growth factor (NGF), brain-derived neurotrophic factor (BDNF), neurotrophin-3 (NT-3), neurotrophin-4 (NT-4), members of the glial cell line-derived neurotrophic factor ligands (GDNF) and ciliary neurotrophic factor (CNTF). In some embodiments, the protein of interest is neublastin. It also should be appreciated, that analytical techniques described herein can be applied to other materials or samples (for example for chemical syntheses) where one or more molecules (e.g., chemical stocks) are subject to isomerization which would alter their vibrational properties.

In some embodiments, a protein of interest may be, but is not limited to, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab, Tildrakizumab, Tigatuzumab, TNX-, Tocilizumab, Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

In some embodiments, a Raman spectroscopy may be performed in the visible, near infrared, infrared, near ultraviolet, or ultraviolet (UV) range. In some embodiments, a signal enhancement technique known as Surface Enhanced Raman Spectroscopy (SERS), which relies on a phenomenon known as surface plasmonic resonance, may be used. In some embodiments, resonance Raman spectroscopy, tip-enhanced Raman spectroscopy, polarized Raman spectroscopy, stimulated Raman spectroscopy, transmission Raman spectroscopy, spatially offset Raman spectroscopy, Fourier Transform (FT) Raman, or hyper Raman spectroscopy may be used. In some embodiments, a Raman analyzer can be used that is configured with a laser or other suitable light source that operates at appropriate wavelengths (e.g., 325 nm, 514.5 nm, 532 nm, 632.8 nm, 647 nm, 752 nm, 785 nm, 830 nm, 1064 nm, etc.)

In some embodiments, data fusion may be used to augment the spectroscopic analysis. For example, a second spectroscopic analysis (e.g., Nuclear Magnetic Resonance (NMR), X-Ray Fluorescence (XRF), Small Angle X-Ray Scattering (SAXS), Powder Diffraction, Near Infrared Spectroscopy (NIR), or Fourier Transform Infrared Spectroscopy (FTIR)) may be performed to obtain a second spectrum of a lot sample, and data fusion analysis may be used to evaluate the lot sample.

In one aspect, the disclosure provides a method of defining a Raman signature of a cell culture material, the method comprising obtaining a Raman spectrum of a cell culture material (e.g., in a non-interfering or minimally-interfering solution, for example in water, an aqueous buffer, or other solvent) and evaluating one or more attributes (e.g., peak attributes) of the Raman spectrum that are associated with desired or undesired cell culture outcomes.

In some embodiments, only a portion of the Raman spectrum is evaluated. For example, data relating to only a portion of the Raman spectrum is evaluated and the remaining data is filtered or otherwise removed prior to analysis.

In one aspect, a Raman spectrum of a cell culture material in a non-interfering or minimally-interfering solution is obtained. A non-interfering or minimally-interfering solution is a solution that allows for the generation of a Raman spectrum of the material (e.g., yeastolate or pluronic) with little to no interference of the material with other agents in the solution. In some embodiments, a non-interfering or minimally-interfering solution would be water, which may or may not have additional non-interfering or minimally-interfering components, such as buffers or salts.

In some embodiments, Raman spectra are obtained for a material of interest (e.g., yeastolate or pluronic) dissolved in a simple solvent such as water (e.g., distilled and/or deionized water), for example by using an excitation laser. In some embodiments, Raman spectra will be obtained for a plurality of samples of a particular material at a plurality of concentrations. In some embodiments, a library or database of Raman spectra can be assembled to cover a range of concentrations that represents a reasonable approximation of the experimental range (e.g., the concentration range of the material in a culture medium). Thus, for instance, Raman spectra may be obtained from the same material at different concentration increments, such as 0.1 g/L. The data obtained by using these Raman spectra are analyzed, including derivatizing and normalizing of the data if needed. Computer programs, including statistical software, may be used in this process. In some embodiments, the data analysis results in peaks in the Raman spectrum that represent the basis peaks for evaluating the material of interest.

In some embodiments, Raman spectra are also obtained for various concentrations of a material of interest (e.g., yeastolate, or pluronic) added to culture medium of interest. It should be appreciated that the culture medium of interest may have a variety of make ups. However, the culture medium of interest ideally should mimic closely the biological production culture medium and should include the major components present in cell culture media (polypeptide, sugars, salts, nucleic acids, cellular debris, and nutrients). The peaks identified in the Raman spectra of the material in the non-interfering or minimally-interfering solution can be used to identify peaks in the Raman spectra of the material in the culture medium. In some embodiments, the spectra of the material of interest (e.g., yeastolate or pluronic) in the culture medium are trimmed to match one or more peaks previously identified in the Raman spectra of the material of interest in the non-interfering or minimally-interfering solution. In some embodiments, the spectra are trimmed by removing peaks that are distorted. In some embodiments, peaks that are distorted are peaks that are laterally shifted or inverted (e.g., in the culture medium). However, it should be appreciated that in some embodiments, distortetd peaks of a material in a culture medium can be used as a reference to compare to other material in the same culture medium. The presence or absence of a difference (e.g., a statistically significant difference) between a spectrum of an unknown material (e.g., a new batch or lot of a cell culture material) relative to a known material (e.g., a material known to have desirable properties for cell growth and/or protein production) can be used as a basis for either using or discarding (e.g., not using) a material for cell growth or protein production.

In some embodiments, the Raman signature of a culture material (e.g., in a simple solution or in a more complex solution such as a culture medium) can be analyzed by building a predictive model based on a multivariate analysis (e.g., a predictive PLS model).

Accordingly, in one aspect the disclosure provides Raman signatures of cell culture materials. In some embodiments, the Raman signature comprises a selected number of peaks and associated peak ranges that allow for the evaluation (e.g., identification and/or comparison) of one or more culture materials with a corresponding reference material. In some embodiments, the Raman signature comprises a selected number of peaks and associated peak ranges (e.g., that are informative for the material of interest because they differ for different types, sources, qualities, or other properties of the material that impact cell culture and/or protein production). In some embodiments, a Raman signature of a culture material comprises multiple combinations of informative peaks. It should be appreciated that a minimal number of peaks may define a Raman signature. However, additional peaks may help refine the Raman signature. Thus, for instance, evaluating a Raman signature consisting of 1, 2, 3, 4 or more peaks (e.g., one or more of peaks A to H in FIG. 1) may provide a high degree of certainty (e.g., 85%, 90%, 95% or higher) that a cell culture grown using a material having an acceptable Raman signature will have good qualities (e.g., a good recombinant protein yield). However, a Raman signature consisting of additional peaks (e.g., 5-10 peaks or more) may provide a higher certainty (e.g., 99%) of good cell culture properties.

In some embodiments, a Raman spectrum of pluronic is evaluated in one or more of the following Raman shift ranges: 845 $cm^{-1}$ to 872 $cm^{-1}$, 1115 $cm^{-1}$ to 1162 $cm^{-1}$, 1224 $cm^{-1}$ to 1242 $cm^{-1}$, 1265 $cm^{-1}$ to 1325 $cm^{-1}$, 1429 $cm^{-1}$ to 1497 $cm^{-1}$, and/or 2844 $cm^{-1}$ to 3074 $cm^{-1}$. In some embodiments, a Raman spectrum of pluronic is evaluated in one or more of the following Raman shift ranges: 800 $cm^{-}$-900 $cm^{-1}$, 900 $cm^{-1}$-950 $cm^{-1}$, 1000 $cm^{-1}$-1100 $cm^{-1}$, 1100 $cm^{-1}$-1150 $cm^{-1}$, 1150 $cm^{-1}$-1200 $cm^{-1}$, 1250 $cm^{-1}$-1300 $cm^{-1}$, 1300 $cm^{-1}$-1400 $cm^{-1}$, or 1400 $cm^{-1}$-1500 $cm^{-1}$.

In some embodiments, a Raman spectrum of yeastolate is evaluated in one or more of the following Raman shift ranges: 1136 $cm^{-1}$ to 1210 $cm^{-1}$, 1324 $cm^{-1}$ to 1367 $cm^{-1}$, 1388 $cm^{-1}$ to 1462 $cm^{-1}$, 1585 $cm^{-1}$ to 1684 $cm^{-1}$, 1714 $cm^{-1}$ to 1805 $cm^{-1}$, and/or 2865 $cm^{-1}$ to 2954 $cm^{-1}$.

Accordingly, a signature for pluronic or yeastolate can be based on one or more peaks within one or more of the wavenumber ranges described above.

In some embodiments, the regions being analyzed for a particular material (e.g., one or more of the regions identified above for pluronic or yeastolate) can be used to build one or more multivariate models (e.g., PCA and/or PLS and/or other multivariate models) that are sensitive to small changes in the polymerization of the pluronic molecule, or small changes in the composition of the yeastolate. In some embodiments, using PCA, the regions mentioned can be used to evaluate relative peak intensities, peak location (wavenumber) and peak broadness and compare them to known successful lots. In this way, these regions can qualify a lot as similar to or different from desirable lots with a change of less than 5% in the measured material. Analyses can be carried out at normal process concentrations ranging from 0.5 to 5 g/L, however greater sensitivity is seen at higher concentrations.

In one aspect, the disclosure provides methods for evaluating a cell culture material (e.g., a nutrient material) by generating a reference library of Raman signatures of materials that are associated with one or more quality parameters of a cell culture using that material. For instance, Raman signatures can be generated from materials that are known to result in a biological production process with a good yield, and Raman signatures can be generated from materials that are associated with a low yield. A Raman spectrum can subsequently be taken for a material being considered for use (e.g., a lot or batch of a cell culture material) and be parsed with the library of Raman signatures to determine whether it should be used or not.

In some embodiments, one or more attributes of a peak, e.g., in a particular region, can be a basis for excluding material. In some embodiments, at least a 5%, 10%, 15%, 20%, 25%, 30%, 35%, 40%, 45%, 50%, 55%, 60%, 65%, 70%, 75%, 80%, 85%, 90%, or 95% difference in one or more peak attributes (e.g., peak height, peak area, peak width) compared with an appropriate control can be a basis for excluding material. In some embodiments, at least a 5%, 10%, 15%, 20%, 25%, 30%, 35%, 40%, 45%, 50%, 55%, 60%, 65%, 70%, 75%, 80%, 85%, 90%, or 95% difference (e.g., decrease, increase) in peak height compared with an appropriate control can be a basis for excluding material. In some embodiments, at least a 5%, 10%, 15%, 20%, 25%, 30%, 35%, 40%, 45%, 50%, 55%, 60%, 65%, 70%, 75%, 80%, 85%, 90%, or 95% difference (e.g., decrease, increase) in the area under the curve (AUC) within the region of a peak in a Raman spectrum compared with an appropriate control can be a basis for excluding material.

Examples of cell culture materials that can be evaluated using techniques described herein include, but are not limited to, nutrient materials (e.g., yeastolate), Pluronic, and other materials that are included in a cell culture medium.

Yeastolate is a yeast extract (e.g., an aqueous yeast extract) that can be obtained through autolysis of yeast. Yeastolate can be used for cell growth. However, batch to batch or lot to lot variation can produce different cell growth results. It should be appreciated that different sources or lots of yeastolate can be assayed as described herein.

Pluronic is a tri-block co-polymer comprising poly (propylene oxide) (PPO) and poly (ethylene oxide) (PEO). In certain embodiments, the tri-block co-polymer is poloxamer P188, which is marketed by BASF under the trade name PLURONIC® F68. Other tri-block co-polymers that may assessed using methods disclosed herein include, but are not limited to, PLURONIC® 10R5, PLURONIC® 17R2, PLURONIC® 17R4, PLURONIC® 25R2, PLURONIC® 25R4, PLURONIC® 31R1, PLURONIC® 10R5, PLURONIC® F108, PLURONIC® F127, PLURONIC® F38, PLURONIC® F68, PLURONIC® F77, PLURONIC® F87, PLURONIC® F88, PLURONIC® F98, PLURONIC® L10, PLURONIC® L101, PLURONIC® L121, PLURONIC® L31, PLURONIC® L35, PLURONIC® L43, PLURONIC® L44, PLURONIC® L61, PLURONIC® L62, PLURONIC® L64, PLURONIC® L81, PLURONIC® L92, PLURONIC® N3, PLURONIC® P103, PLURONIC® P104, PLURONIC® P105, PLURONIC® P123, PLURONIC® P65, PLURONIC® P84, and PLURONIC® P85. However, it should be appreciated that other tri-block co-polymers having different relative amounts of PPO and PEO can be assayed as described herein.

Aspects of the methods disclosed herein may be implemented in any of numerous ways. For example, the various methods or processes outlined herein may be coded as software that is executable on one or more processors that employ any one of a variety of operating systems or platforms. Such software may be written using any of a number of suitable programming languages and/or programming or scripting tools, and also may be compiled as executable machine language code or intermediate code that is executed on a framework or virtual machine. The MATLAB® signaling processing toolbox (The MathWorks, Inc., Natick, Mass.) is an exemplary, but non-limiting, system that may be used for implementing certain aspects of the methods disclosed herein.

In this respect, aspects of the disclosure may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the disclosure. The computer readable medium or media can be transportable, such that the program or programs stored thereon can be loaded onto one or more different computers or other processors to implement various aspects of the present disclosure.

The terms "program" or "software" are used herein in a generic sense to refer to any type of computer code or set of computer-executable instructions that can be employed to program a computer or other processor to implement various aspects of the present disclosure. Additionally, it should be appreciated that according to one aspect of this embodiment, one or more computer programs, which when executed perform certain methods disclosed herein, need not reside on a single computer or processor, but may be distributed in a modular fashion among or between a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element or a list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Words or phrases defined herein shall have the meanings herein ascribed unless an alternative meaning is clearly apparent from the language or context in which the word or phrase is used. Moreover, definitions provided for a word or phrase in one tense or form shall apply to other tenses or forms of the word or phrase.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference, in particular for the teaching that is referenced herein.

Examples

The following examples illustrate some of the non-limiting results obtained by applying Raman spectroscopic analysis to raw materials.

FIG. 1 illustrates Raman spectra of several pluronic samples. Raman data were obtained using a Kaiser RXN2 analyzer with "bIO-Pro" (SIC) optics and configured with a CCD detector. The RXN2 was equipped with a 785 nm continuous wave laser. A holographic notch filter is used to reject Rayleigh scattering, HSG-785-LF/HSG-785-HF gratings (for low and high frequency windows). Laser power was set to 400 mW. Integration time and total collection time were set appropriately. Samples were prepared as liquid based mixtures using distilled water.

The spectra are shown between 800 and 1500 cm$^{-1}$. The Raman spectrum for each sample is depicted as a separate line plot in the graph. Multiple peaks, denoted A-H, were identified that discriminate the sample labeled as n with other samples. For example, the sample labeled as n has discernible differences in peak attributes compared with the sample labeled as m at each of peaks A-H. Accordingly, one or more of peak regions A-H may be evaluated as described herein. The sample labeled as n is pluronic F127 (poloxamer 407). The other samples, including the sample labeled as m, is pluronic F68 (poloxamer 188).

Figure 2:
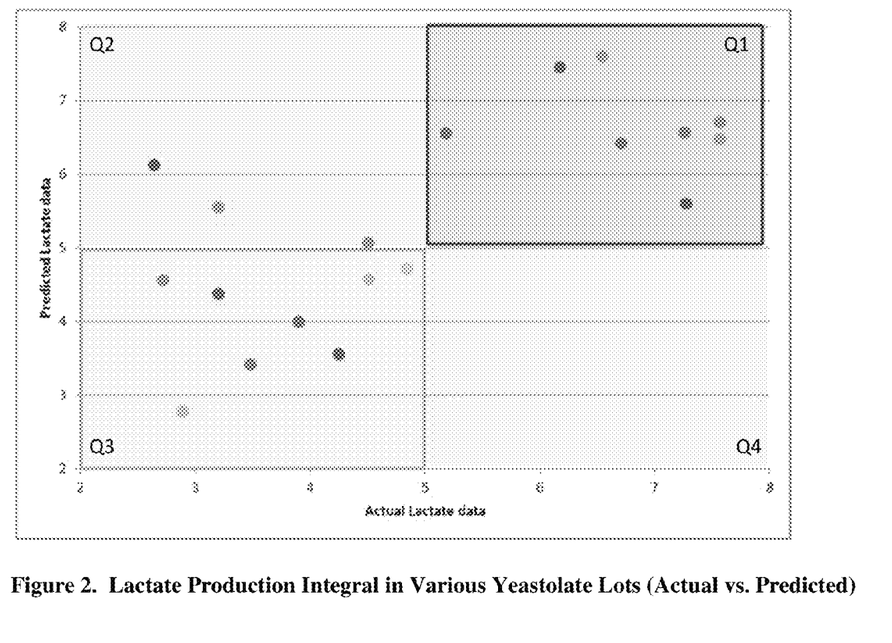
FIG. 2 illustrates a non-limiting embodiment of lactate production integral for several yeastolate lots (Actual vs. Predicted)

FIG. 2 illustrates lactate production integral of various yeastolate lots, as predicted by a Raman-based model and as observed in actual use. For the cell culture processes illustrated in FIG. 2, it is assumed (e.g., based on data collected from actual cell culture processes) that process performance is acceptable when the Lactate Production Integral value is between 2 and 5 (a "low" value). Lactate Production Integral correlates well to Peak 5 and therefore levels of Gal (galactosylation) isoforms. Galactosylation is the glycosylation of a protein with a galactose molecule. This post-translational modification is associated with the bioactivity of some proteins and its level can be used to evaluate bioactivity of a protein sample. Quadrant 3 (Q3) shows different lots of yeastolate that were predicted to have low lactate levels (based on the model) and actually had low lactate levels. Quadrant 1 (Q1) shows lots of yeastolate that were predicted to have high lactate levels (based on the model) and actually had high lactate levels. Thus, the model correctly predicted that the lots in Q3 should be accepted and the lots in Q1 should be rejected. Quadrant 2 (Q2) shows yeastolate lots in which low lactate was predicted, but high lactate was actually observed. Thus, Q2 represents false positive predictions, which correspond to over-rejection of yeastolate lots. Quadrant 4 (Q4), which is empty, represents false negative predictions, which correspond to over-acceptance of yeastolate lots.

Figure 3:
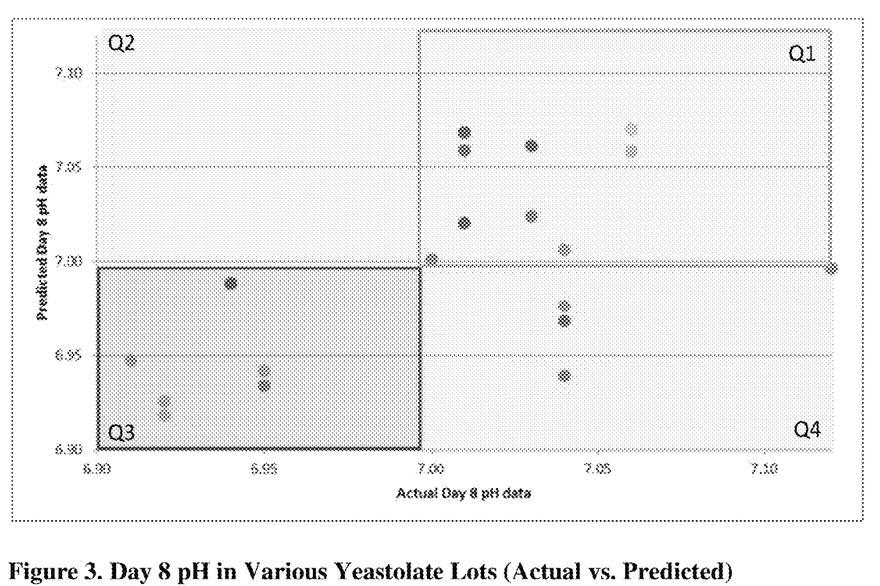
FIG. 3 illustrates a non-limiting embodiment of Day 8 pH for several yeastolate lots (Actual vs. Predicted)

FIG. 3 illustrates Day 8 pH of various yeastolate lots, as predicted by a Raman-based model and as observed in actual use. For the cell culture process illustrated in FIG. 3, it is assumed (e.g., based on data collected from actual cell culture processes) that process performance is acceptable when the Day 8 pH value is between 7.00 and 7.10 (a "high" value). Day 8 pH correlates well to Peak 5 and therefore levels of Gal isoforms. Q1 shows lots of yeastolate which are correctly predicted (based on the model) to have high Day 8 pH levels. Q3 shows lots of yeastolate which are correctly predicted (based on the model) to have low Day 8 pH levels. Thus, the model correctly predicts that the lots in Q1 should be accepted and the lots in Q3 should be rejected. Q4 shows yeastolate lots in which low Day 8 pH was predicted, but high Day 8 pH was actually observed. Thus, Q4 represents false positive predictions, which correspond to over-rejection of lots with high Day 8 pH. Q2, which is empty, represents false negative predictions, which correspond to over-acceptance of lots with low Day 8 pH.

Figure 4:
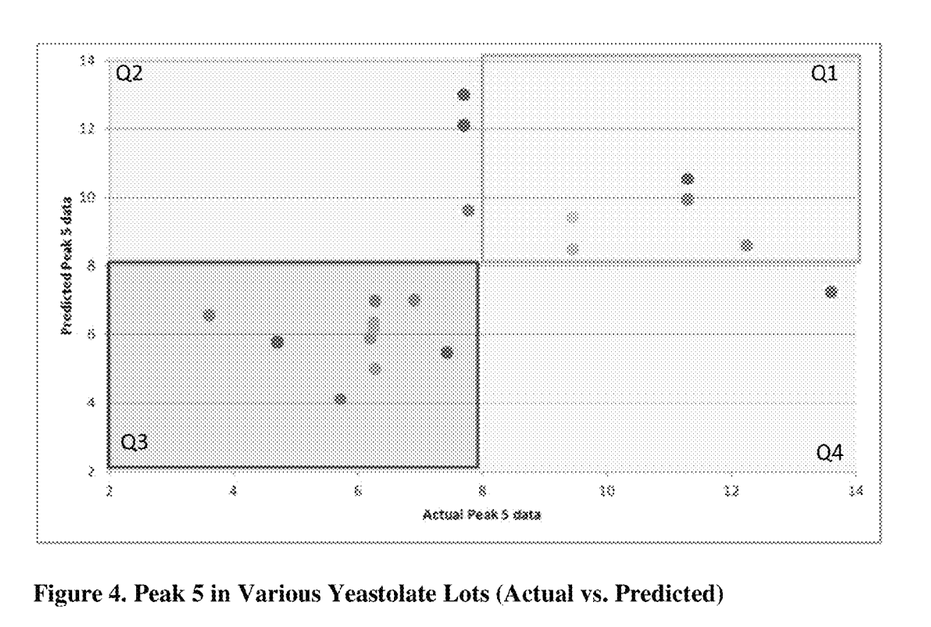
FIG. 4 illustrates a non-limiting embodiment of Peak 5 for several yeastolate lots (Actual vs. Predicted)

FIG. 4 illustrates Peak 5 of various yeastolate lots, as predicted by a Raman-based model and as observed in actual use. For the cell culture process illustrated in FIG. 4, it is assumed (e.g., based on data collected from actual cell culture processes) that process performance is acceptable when the Peak 5 value is between 8 and 14 (a "high" value). Peak 5 correlates well to levels of Gal isoforms. Q1 shows lots of yeastolate which are correctly predicted (based on the model) to have high Peak 5 values. Q3 shows lots of yeastolate which are correctly predicted (based on the model) to have low Peak 5 values. Thus, the model correctly predicts that the lots in Q1 should be accepted and the lots in Q3 should be rejected. Q4 shows yeastolate lots in which low Peak 5 was predicted, but high Peak 5 was actually observed. Thus, Q4 represents false positive predictions, which correspond to over-rejection of lots with high Peak 5. Q2 represents false negative predictions, which correspond to over-acceptance of lots with low Peak 5.

TABLE 1

Statistical analysis for the models of FIGS. 2-4.

| | Percent Error for the Raman Model | | |
|---|---|---|---|
| | Lactate | Day 8 pH | Peak 5 |
| Average | 26.19% | 0.50% | 2.17% |
| Standard Deviation | 31.66% | 0.47% | 1.76% |

Table 1 summarizes the accuracy of the models of FIGS. 2-4. The accuracy of the lactate production integral model is likely lower than the others due to the more variable nature of the input data when compared to the day 8 pH and peak 5. There is a strong correlation between day 8 pH and peak 5, so we expect low error when building a prediction set based on these, however the relationship is weaker with lactate. The data could be improved if a key region of the lactate integral were identified for use in statistical analysis.

Figure 5:
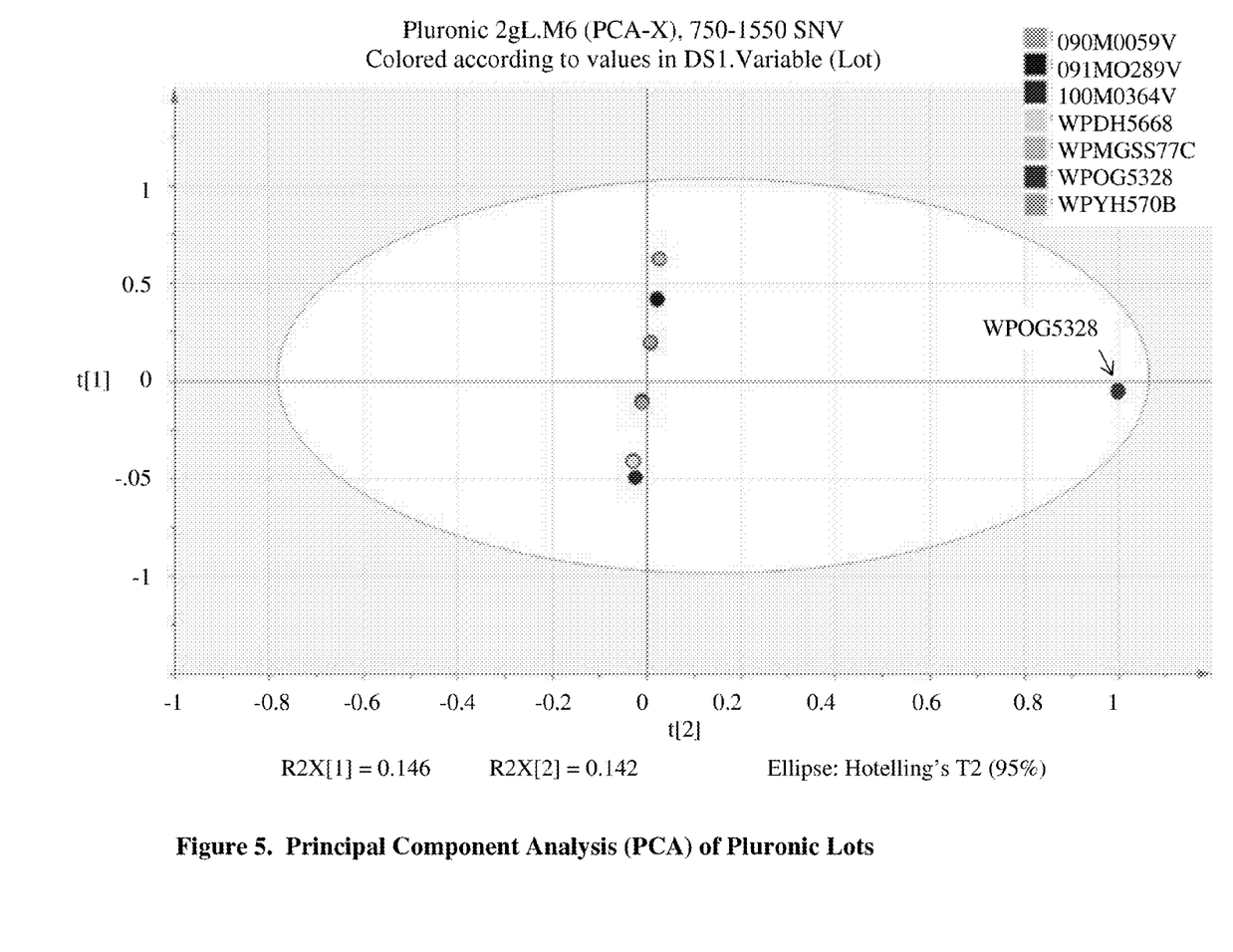
FIG. 5 illustrates a non-limiting embodiment of Principal Component Analysis (PCA) of several pluronic lots.

FIG. 5 illustrates the results of applying PCA to pluronic lots. The clear separation to the right of the purple lot (WP0G5328) is an indicator of a material difference that can be used to qualify new lots prior to use.

In some embodiments, a Raman spectrum of pluronic is evaluated in one or more of the following Raman shift ranges: 845 cm$^{-1}$-872 cm$^{-1}$ (e.g. corresponding to a $CH_2$ rock peak assignment), 1115 cm$^{-1}$-1162 cm$^{-1}$ (e.g. corresponding to a C—O stretch peak assignment), 1224 cm$^{-1}$-1242 cm$^{-1}$ (e.g. corresponding to a $CH_2$ twist peak assignment), 1265 cm$^{-1}$-1325 cm$^{-1}$, 1429 cm$^{-1}$-1497 cm$^{-1}$ (e.g. corresponding to $CH_2$ scissor (×2) peak assignments), and/or 2844 cm$^{-1}$-3074 cm$^{-1}$ (e.g. corresponding to CH stretch (many) peak assignments). In some embodiments, a Raman spectrum of pluronic is evaluated in one or more of the following Raman shift ranges: 800 cm$^{-1}$-900 cm$^{-1}$, 900 cm$^{-1}$-950 cm$^{-1}$, 1000 cm$^{-1}$-1100 cm$^{-1}$, 1100 cm$^{-1}$-1150 cm$^{-1}$, 1150 cm$^{-1}$-1200 cm$^{-1}$, 1250 cm$^{-1}$-1300 cm$^{-1}$, 1300 cm$^{-1}$-1400 cm$^{-1}$, or 1400 cm$^{-1}$-1500 cm$^{-1}$. In some embodiments, a Raman spectrum of yeastolate is evaluated in one or more of the following Raman shift ranges: 1136 $cm^{-1}$-1210 $cm^{-1}$, 1324 $cm^{-1}$-1367 $cm^{-1}$, 1388 $cm^{-1}$-1462 $cm^{-1}$, 1585 $cm^{-1}$-1684 $cm^{-1}$, 1714 $cm^{-1}$-1805 $cm^{-1}$, and/or 2865 $cm^{-1}$-2954 $cm^{-1}$.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method of evaluating a nutrient material, the method comprising:
    performing a Raman spectroscopic analysis on a sample of the nutrient material to obtain a Raman spectrum; and
    identifying a value of a quality parameter based on the Raman spectrum, the quality parameter relating to the nutrient material or to a cell culture grown using the nutrient material, wherein the quality parameter is a Day 8 pH or a Peak 5 or a Lactate Production Integral.

2. The method of claim 1, further comprising:
    differentiating the nutrient material from a second nutrient material based on a difference between the Raman spectrum of the nutrient material and a second Raman spectrum of the second nutrient material.

3. The method of claim 1, further comprising:
    performing a comparison of at least a portion of the Raman spectrum with at least a portion of a model Raman spectrum.

4. The method of claim 3, further comprising:
    based on a result of the comparison, accepting the nutrient material for use in a cell culture process.

5. The method of claim 3, further comprising:
    based on a result of the comparison, rejecting the nutrient material for use in a cell culture process.

6. The method of claim 1, further comprising:
    performing a comparison of data obtained from the Raman spectrum with model data.

7. The method of claim 1, wherein:
    performing the Raman spectroscopic analysis comprises performing Surface Enhanced Raman Spectroscopy (SERS).

8. The method of claim 1, wherein:
    performing the Raman spectroscopic analysis comprises performing ultraviolet (UV) Raman spectroscopy.

9. The method of claim 1, further comprising:
    performing a second spectroscopic analysis on a sample of the nutrient material to obtain a second spectrum; and
    performing a data fusion analysis to evaluate the Raman spectrum.

10. The method of claim 9, wherein the second spectroscopic analysis is a Nuclear Magnetic Resonance (NMR) analysis or a Near Infrared Spectroscopy (NIR) analysis.

11. The method of claim 1, wherein the method further comprises predicting a value of the quality parameter based on a predictive least squares (PLS) predictive model.

12. A method of evaluating a nutrient material, the method comprising:
    performing a Raman spectroscopic analysis on a sample of the nutrient material to obtain a Raman spectrum; and identifying a value of a quality parameter based on the Raman spectrum, the quality parameter relating to the nutrient material or to a cell culture grown using the nutrient material, wherein the quality parameter is a Day 8 pH.

13. A method of evaluating a nutrient material, the method comprising: performing a Raman spectroscopic analysis on a sample of the nutrient material to obtain a Raman spectrum; and identifying a value of a quality parameter based on the Raman spectrum, the quality parameter relating to the nutrient material or to a cell culture grown using the nutrient material, wherein the quality parameter is a Peak 5.

14. A method of evaluating a nutrient material, the method comprising: performing a Raman spectroscopic analysis on a sample of the nutrient material to obtain a Raman spectrum; and identifying a value of a quality parameter based on the Raman spectrum, the quality parameter relating to the nutrient material or to a cell culture grown using the nutrient material, wherein the quality parameter is a Lactate Production Integral.

* * * * *